United States Patent [19]

Lieber

[11] Patent Number: 4,560,464
[45] Date of Patent: Dec. 24, 1985

[54] STICK-ON-MASK FOR USE WITH COULOMETRIC MEASURING INSTRUMENTS

[76] Inventor: Sidney Lieber, 426 E. Shore Rd., Great Neck, N.Y. 11024

[21] Appl. No.: 553,546

[22] Filed: Nov. 21, 1983

Related U.S. Application Data

[63] Continuation of Ser. No. 244,693, Mar. 17, 1981, abandoned.

[51] Int. Cl.$^4$ ............................................. G01N 27/46
[52] U.S. Cl. ..................... 204/434; 204/1 T; 204/279; 204/400; 204/129.65
[58] Field of Search ................. 204/1 T, 129.65, 400, 204/434, 279

[56] References Cited

U.S. PATENT DOCUMENTS

| | | | |
|---|---|---|---|
| 2,319,196 | 5/1943 | Anderson et al. | 204/434 |
| 2,457,234 | 12/1948 | Herbert et al. | 204/434 |
| 3,012,958 | 12/1961 | Vixler | 204/197 |
| 3,139,394 | 6/1964 | Oelgoetz | 204/129.65 |
| 3,410,772 | 11/1968 | Geld et al. | 204/196 |
| 3,467,592 | 9/1969 | Eisberg et al. | 204/129.6 |
| 4,274,418 | 6/1981 | Vesterager et al. | 204/403 |
| 4,310,389 | 1/1982 | Harbulak | 204/434 |

FOREIGN PATENT DOCUMENTS 0098973 8/1976 Japan ........................ 204/129.65

*Primary Examiner*—T. Tung
*Attorney, Agent, or Firm*—Nims Howes Collison & Isner

[57] ABSTRACT

A mask for precisely defining the area of a thin metal layer on a substrate to be deplated during measurement of the thickness of the thin metal layer utilizing a coulometric technique. The mask having an adhesive on one side for securing the mask to the thin metal layer and for preventing the leakage of electrolyte between the mask and the thin metal layer.

2 Claims, 5 Drawing Figures

STICK-ON-MASK FOR USE WITH COULOMETRIC MEASURING INSTRUMENTS

This is a continuation of application Ser. No. 244,693, filed Mar. 17, 1981, now abandoned.

BACKGROUND OF INVENTION

This invention relates to an improvement in apparatus for measuring the thickness of a thin metal coating on a substrate utilizing a coulometric technique.

Conventional coulometric measuring instruments utilize an electrolytic cell to electrolytically strip a thin metal coating on a substrate in making a measurement. The electrolytic cell includes a container for the electrolyte and a gasket having a central opening in fluid communication with the interior of the electrolyte container. In using this type of apparatus, the electrolyte container and the gasket are held against the plated substrate and the container filled with electrolyte. Sufficient force is applied to the container to prevent leakage of the electrolyte between the gasket and the workpiece. With this apparatus the electrolyte is held in intimate contact with the thin metal layer located within the central opening of the gasket. The gasket in conventional apparatus provides two functions—first, containment of the electrolyte and second, defining the area to be deplated. The electrolytic cell further includes a cathode within the interior of the container connected to a current source providing a known current. The workpiece is also connected to the current source, such that the workpiece is the anode of electrolytic cell, thus completing the electrical circuit.

Once the electrolytic cell and gasket are in position and filled with electrolyte, the current source is turned on and deplating of the plated layer within the area defined by the gasket commences. The potential across the electrolytic cell is measured on a timed basis. During deplating, this potential is approximately constant. However, once the metal layer is deplated, the potential abruptly changes to a different potential. The time from when the current source is turned on to when the potential so changes is indicative of the plating thickness. The time is converted to units of thickness by apparatus connected to the electrolytic cell.

For more accurate results, it is common to agitate the electrolyte to remove the bubbles forming on the metal layer being deplated and to prevent localized depletion of the electrolyte. If the bubbles are not removed or if the electrolyte becomes locally depleted, the time required to deplate the metal layer would be increased, thus affecting the accuracy of the measurement. Bubbles prevent the electrolyte from being in intimate contact with the metal layer, and depletion of the electrolyte severely alters the deplating conditions.

In conventional coulometric measuring instruments, the gasket is generally formed of a resilient material to achieve a leakage-free seal around the edge of the gasket when the electrolyte container is brought into engagement with the gasket and pressed against the workpiece. A conventional electrolytic cell with a gasket is shown in FIG. 1. The gasket shown has a minimum dimension A required to achieve sufficient rigidity to consistently maintain the critical dimention B defining the diameter of the area to be deplated when the gasket is pressed against the workpiece. There is an annular region C adjacent the outer edge of the area being deplated which is relatively stagnant because it does not receive the same degree of agitation as the center of the area being deplated. Thus, in this region, the benefits of agitation are not partically realized. Furthermore, because of the relatively large dimension A required, there is a practical limitation on the smallest area capable of being deplated for purposes of making a thickness measurement. The reason for this is the inability to properly agitate the entire volume of the electrolyte adjacent to the area being deplated when this volume is small. It has been found desirable to maintain the ratio of A/B to be less than approximately 1.0 to assure proper agitation. In order to maintain the ratio A/B at less than 1.0, the minimum diameter dimension B has been limited in commercial units by the minimum thickness dimension A required to achieve sufficient mechanical rigidity of the gasket necessary to contain the electrolyte and at the same time, accurately define the area to be deplated.

Since the gasket in commercial units available today is resilient, to provide a proper seal between the gasket and the workpiece, it is critical, for accurate, repeatable measurements, for the electrolyte container to be pressed against the gasket with precisely the same force during a single measurement, and further, during subsequent measurements. The reason for this is that the area being deplated changes with the force applied. The variation in area bring deplated affects the time period required to deplate the metal layer and, therefore, the accuracy of the measurement.

Finally, it is not possible with commercially available units to measure workpieces having small radii of curvature because of the distortion of the area being defined by the resilient gasket when an attempt is made to prevent leakage of the electrolyte by increasing the pressure on the gasket against the workpiece.

SUMMARY OF THE INVENTION

The disadvantages and limitations of commercially available coulometric measuring instruments are overcome by the present invention.

The present invention employs a stick-on-mask which has a central aperture for very precisely defining the area to be deplated. The stick-on-mask is made of a flexible, non-resilient, dimensionally stable material such as Kapton. Kapton is a registered trademark of Du Pont de Nemours E. I. & Co. for a polyamide type material manufactured by Du Pont de Nemours E. I. & Co. The mask is preferably constructed with an adhesive on one side for adhesively securing the mask to the workpiece.

The container of the electrolytic cell has a forward cell grommet having a central opening in fluid communication with the interior of the electrolyte container and is constructed of resilient material. The container with the cell grommet is brought into engagement with the mask and sufficient force is applied to prevent leakage of the electrolyte when the container is filled. With a stick-on-mask the area being deplated is precisely defined at all times by the central aperture of the non-resilient, dimensionally stable mask. The adhesive seals the mask on the plated layer to prevent leakage of the electrolyte between the mask and the plated layer, independent of the force applied on the mask through the cell grommet. The force applied has no affect on the size of the central aperature of the mask. Thus, with the present invention, a user need only be concerned with the force necessary to stop any leakage of electrolyte between the cell grommet and the mask. This force does not affect the measurement in any way, which is not the case with conventional coulometric measuring instruments.

Since the area to be deplated with the present invention is defined by the aperture of the stick-on-mask, measurements may be made on much smaller areas than with conventional units utilizing a resilient cell gasket. Since the mask is relatively thin, the electrolyte over the entire area to be deplated may be agitated and the stagnant ring eliminated. Thus, more accurate and reproducible results are obtained and it is possible to measure accurately on workpieces having much smaller areas and smaller radii of curvature than heretofore possible.

Another advantage is that it is now possible to inexpensively fashion the shapes of the mask apertures because it involves only a simple die cut in the mask material. With conventional gaskets, it is necessary to make a new mold for forming entirely new gaskets. Thus, accurate measurements can be made of small and odd shaped areas that could not be measured previously with gaskets having circular apertures now available on the market.

In addition, the operator using the stick-on-mask can more easily align the mask with the specific area which is required to be deplated. This results because the operator can better see the area when a thin stick-on-mask is applied as compared with the situation where a relatively thick gasket is positioned. With a stick-on-mask, the operator may make additional measurements quite close and adjacent to areas previously deplated with no difficulty.

In another application of the present invention, the conventional cell arrangement is replaced with a jet of electrolyte. The jet can be generated by means of a pump or by gravity feed and in either case, the liquid electrolyte can be returned to a large reservoir. The use of a jet achieves the ultimate in effective agitation of the surface of the area being deplated. The jet stream is directed against the stick-on-mask by means of an appropriate nozzle-cathode which serves the dual function of acting as a cathode as well as providing means for directing the stream of electrolyte onto the area to be deplated as defined by the aperture of the stick-on-mask. Since gravity is not required to hold the electrolyte against the workpiece, the jet may be directed either vertically, or horizontally in any direction as required which has a particularly useful application when large or heavy parts, which cannot be easily manipulated, are to be measured.

BRIEF DESCRIPTION OF DRAWINGS

In order that the invention may be clearly understood and readily carried into effect, a preferred embodiment will now be described by way of example only, with reference to the accompanying drawings therein.

DESCRIPTION OF A PREFERRED EMBODIMENT

Figure 2:
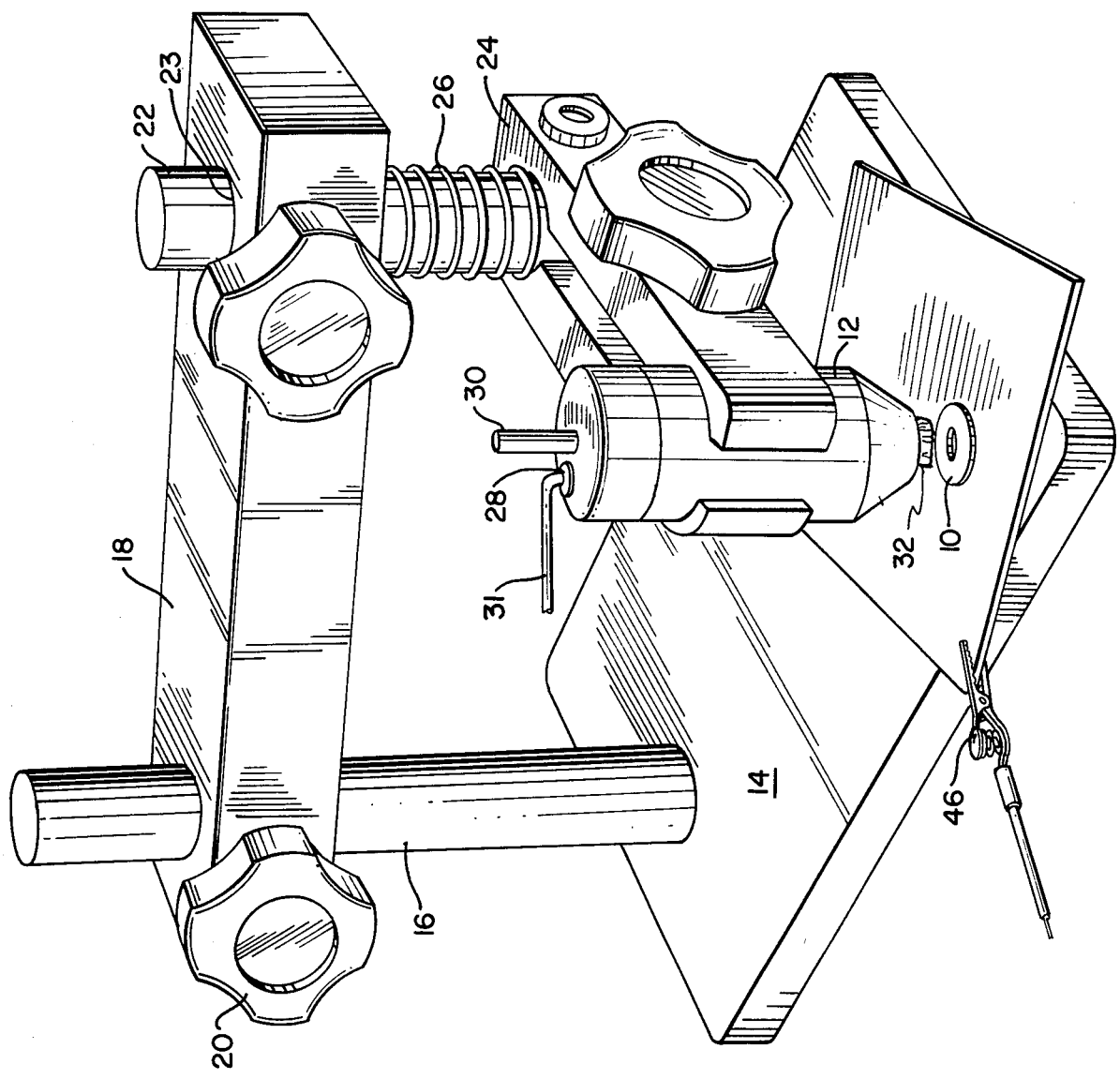
FIG. 2 is a perspective view of a coulometric measuring cell, and holder used with a stick-on-mask according to the present invention.

A stick-on-mask 10 according to the present invention, is shown in FIGS. 2, 3, 4 and 5. A coulometric cell 12 used in conjunction with the stick-on-mask 10 is shown in FIG. 2.

A holder, which is not part of the present invention, is provided to hold the coulometric cell 12 during a measurement as shown in FIG. 2. This holder includes a base 14, an upright standard 16 and an arm 18 having one end slidably mounted on standard 16. The arm 18 is conventionally locked in position on standard 16 with thumb screw 20.

A depending rod 22 is slidably mounted in a bore 23 formed in the other end of arm 18. The arm 18 includes limit means (not shown) for preventing the rod 22 from dropping out of the bore 23. At the lower end of rod 22 is mounted a cell clamp 24 which holds the cell 12. A spring 26 surrounds the rod 22 between the arm 18 and cell clamp 24 biasing the cell clamp 24 downwardly. When the arm 18 is slid downwardly on standard 16 to bring the cell 12 into engagement with a workpiece and the arm 18 secured in this position with a thumb screw 20, the spring 26 assures that the cell 12 is forced against the workpiece with the same force from measurement to measurement.

The coulometric cell 12 includes a terminal 28 for connecting the cathode-agitator tube 30 to a current source (not shown) through lead 31. The cathode-agitator tube 30 extends into the cell 12 and functions as a cathode for the electrolyte cell. Pulsating air may be introduced from a source (not shown) through the tube 30 to agitate the electrolyte during a measurement.

Figure 1:
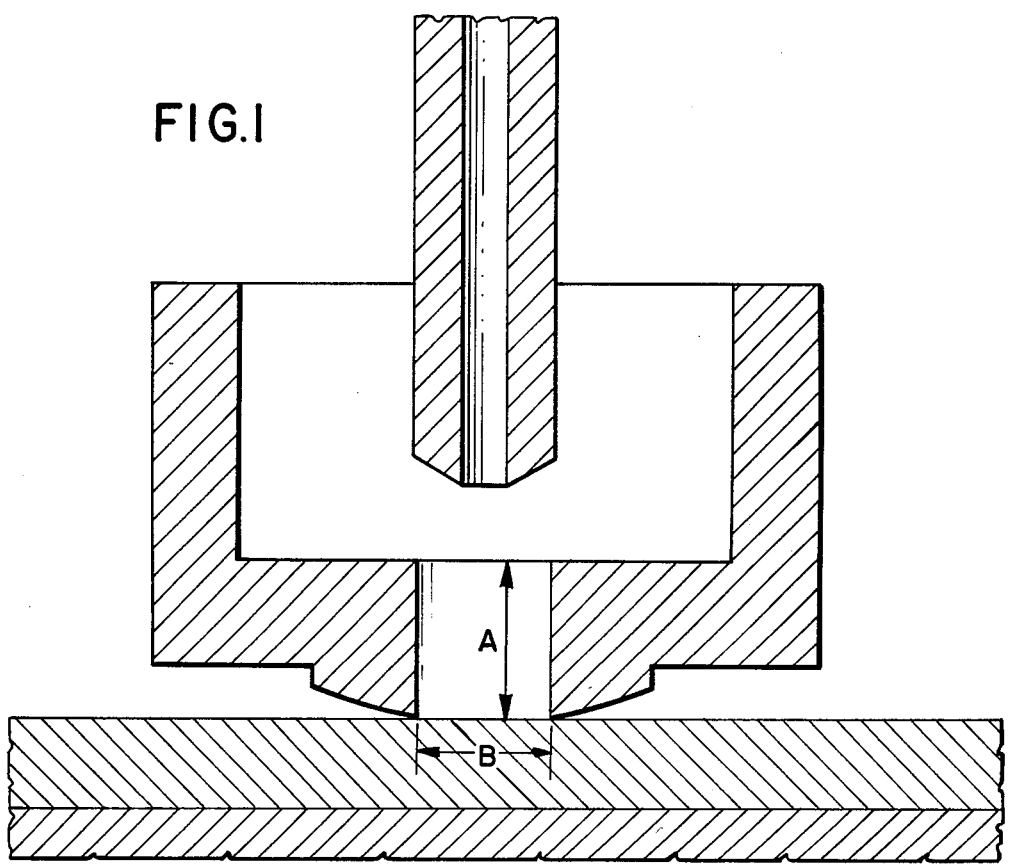
FIG. 1 is a schematic, cross-sectional, elevational, partial view of a conventional coulometric measuring cell.
Figure 3:
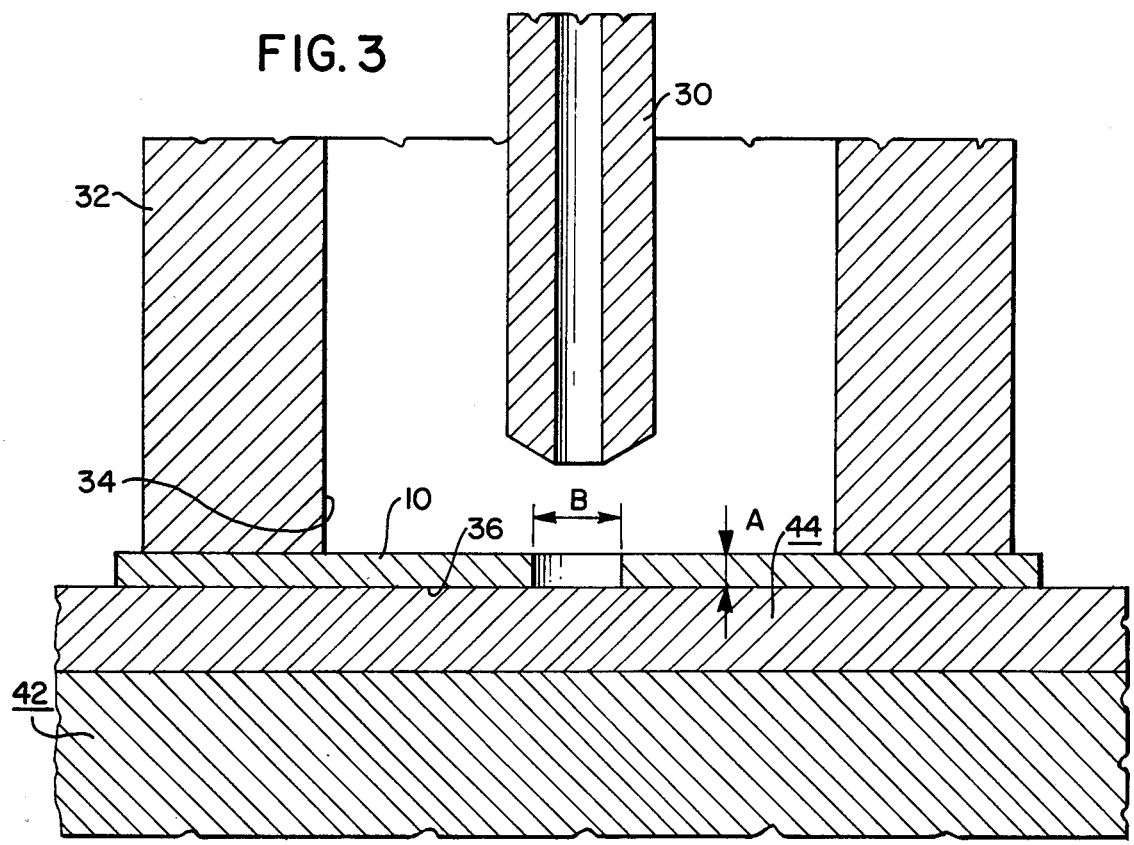
FIG. 3 is a schematic, cross-sectional, elevational, partial view of a coulometric measuring cell and stick-on-mask according to the present invention.

A cell grommet 32 is frictionally secured to the lower end of the coulometric cell 12. This grommet 32 has a central aperture 34 in fluid communication with the interior of cell 12 and provides a sealed interface between the cell and the stick-on-mask 10 as shown in FIG. 3. This grommet 32 functions to prevent leakage of the electrolyte between the grommet 32 and the stick-on-mask 10 during a measurement.

Figure 4:
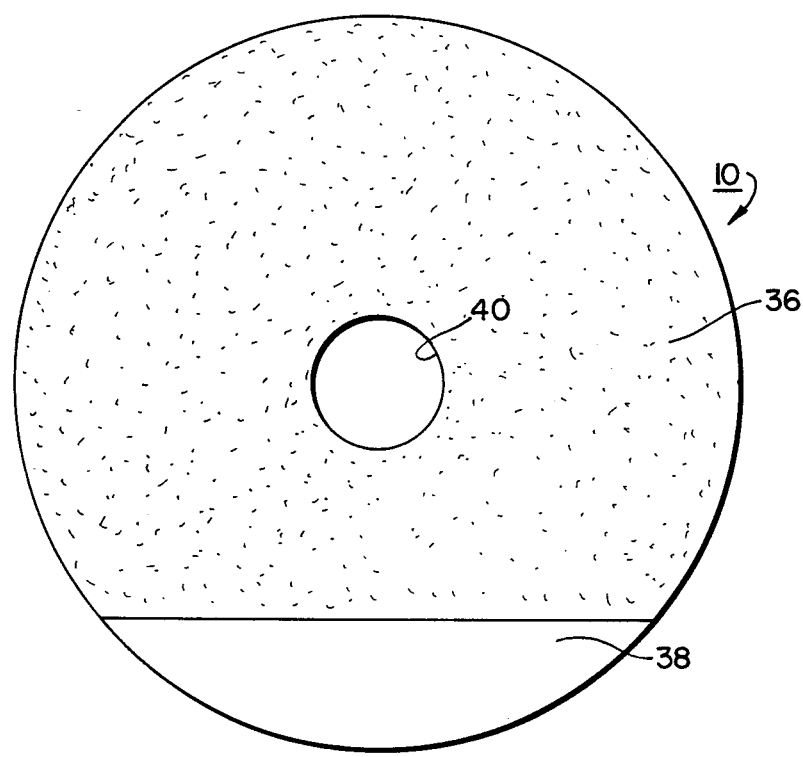
FIG. 4 is a bottom view of the stick-on-mask shown in FIG. 3.

The stick-on-mask 10 used with a coulometric cell 12 is shown in FIGS. 2, 3 and 4. The stick-on-mask 10 includes an adhesive 36 provided on the bottom surface thereof, except, in a preferred embodiment, for a small tab portion 38. The adhesive 36 secures the stick-on-mask 10 to the workpiece during a measurement. By not providing adhesive on tab 38, it is easier for a user to remove the stick-on-mask 10 after a measurement. The adhesive 36 provides a particularly important function when used with the present stick-on-mask 10. By securing the stick-on-mask 10 to the workpiece with the adhesive, there is provided a seal for preventing electrolyte from leaking between the mask and the workpiece independent of the force applied by the user to prevent leakage of the electrolyte between the mask and the cell grommet 32. However, it is contemplated that other means may be used in sealing the mask to the workpiece. Any such other means are considered to be within the scope of the present invention.

The stick-on-mask 10 is constructed of a flexible, non-resilient dimensionally stable material such as Kapton. The stick-on-mask 10 has an aperture 40 which, in the embodiment shown in FIG. 4, is circular. It should be realized, however, that any shaped aperture could be made depending on the particular requirements of the user. A simple die cut is used to form the particular aperture.

A mask has been constructed with the thickness of 0.0004 inch and accurate measurements have been made with an aperture 40 having a diameter of 0.04 inch. The ratio of the mask thickness to the diameter of the aperture 40, in this construction was less than 1.0. It is contemplated that smaller apertures may be used, maintaining the ratio of A/B to be not greater than 1.0, with the stick-on-mask 10 of the present invention.

To make a thickness measurement using a stick-on-mask 10, a user initially positions the stick-on-mask 10 on the workpiece where the measurement is to be made. The adhesive 36 secures the stick-on-mask in this position. If an electrolytic cell is used, the cell 12 with a forward cell grommet 32 is placed in abutting relation with the stick-on-mask 10 with the central aperture 34 of the cell grommet 32 overlapping the aperture 40, as shown in FIG. 3. In a preferred embodiment, the outside diameter of the stick-on-mask 10 is sized to be approximately the same as the outside diameter of the cell grommet 32 so that the central aperture of the cell grommet 32 can be easily aligned with the aperture 40 of the stick-on-mask 10 by making the outside diameter of the stick-on-mask 10 concentric with the outside diameter of cell grommet 32.

The workpiece having a substrate 42 and a plated layer 44 is then connected as an anode to the current source (not shown) with, for example, an alligator clip 46, as shown in FIG. 2. The cell 12 is then filled to the appropriate level with an appropriate electrolyte and the current source turned on. The potential across the electrolytic cell is monitored and the time required from the time the current source is turned on to the time the potential across the electolytic cell changes abruptly is measured. This time is converted to units of thickness by an instrument (not shown) and displayed to the user.

Figure 5:
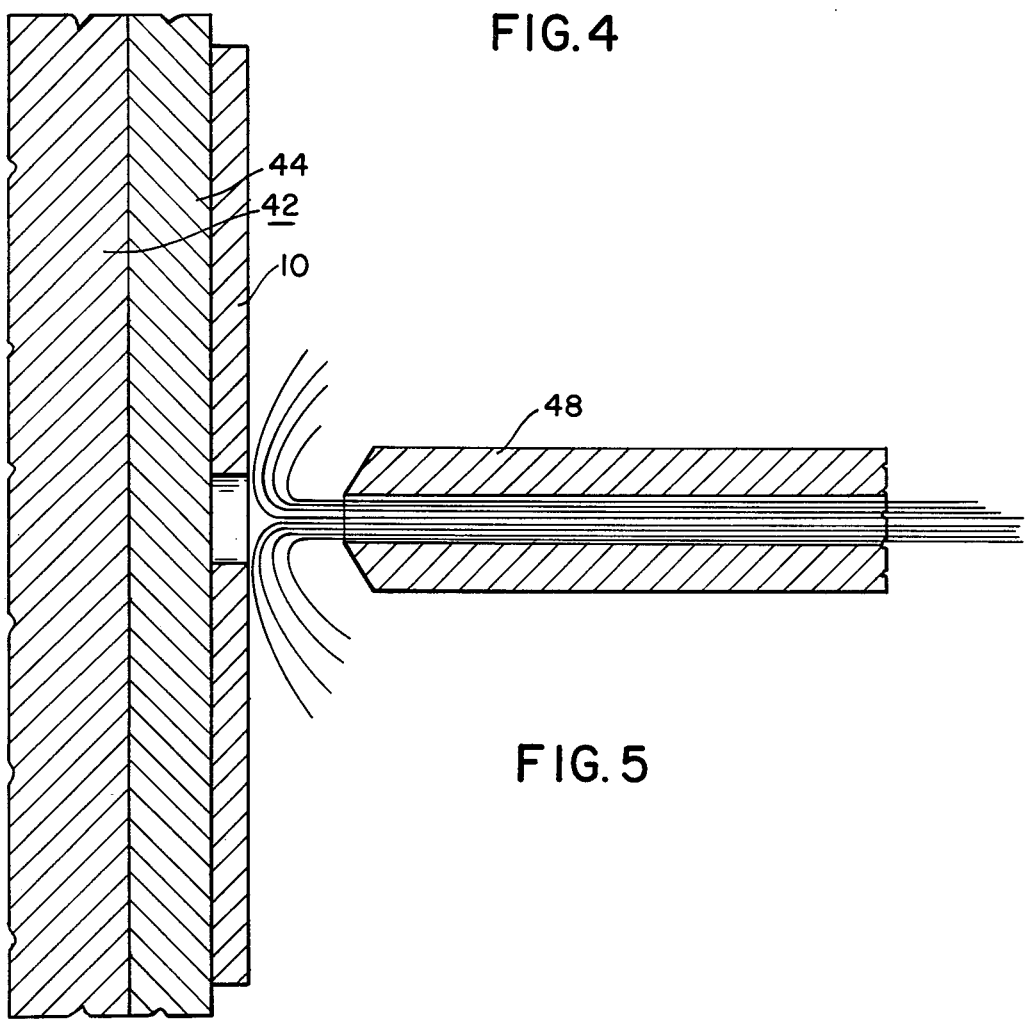
FIG. 5 is a schematic, elevational, partial view of another application of the present invention.

Another application of the stick-on-mask 10 is shown in FIG. 5. The stick-on-mask is secured to the plated layer 44 on substrate 42 of the workpiece where the measurement is to be made. As before, the workpiece is connected to a terminal of the current source (not shown) to be the anode of the electrolytic cell. In this application, a container for the electrolyte need not be used. A tubular nozzle-cathode 48 is connected to the other terminal of the current source and becomes the cathode of the electrolytic cell. Electrolyte is forced through the tubular nozzle-cathode 48 as shown in FIG. 5 and directed at the stick-on-mask 10. The electrolyte is not contained but is directed by gravity to a recycling reservoir.

With this novel configuration, measurements may be made of parts that could not otherwise be measured, due to geometric limitations, with a conventional electrolytic cell having an electrolyte container.

The jet of electrolyte can be generated by a pump or gravity feed. The use of a jet clearly achieves the ultimate in effective agitation at the area being deplated. If a pump is used, it is possible to direct the jet either vertically or horizontally in any direction required, thus making it possible to measure parts which are heavy or large and cannot be easily manipulated. Local measurements of very small areas can be made easily with this configuration where it would be impossible to hold the cell grommet 32 against the stick-on-mask 10. For example, the plating on wire can be measured easily. Normally, plating on wire is measured by immersing a length of the wire in a deplating solution. The plating on this entire length of wire is deplated which gives only an average of the plating thickness along the entire length of the wire being deplated. With the present configuration, a jet of electrolyte can be directed to a specific small area of the wire surface and a measurement made of this small area.

In summary, with the present invention, it is now possible to make accurate, repeatable measurements of thin metal coatings on substrates with the coulometric method when the mask apertures are very small. In addition, with the present invention, a user may make measurements of curved surfaces of much smaller radii of curvature than as heretofore been possible.

While the fundamental novel features of the invention have been shown and described, it should be understood that various substitutions, modifications and variations may be made by those skilled in the art without departing from the spirit or scope of the invention. Accordingly, all such modification and variations are included in the scope of the invention as defined by the following claims.

I claim:

1. For use in coulometric measurement apparatus for determining the thickness of a thin metal coating on a workpiece substrate through timed deplating thereof, said apparatus having
   an electrolyte container,
   grommet means dependent from the base of said electrolyte container and disposed in fluid communication with the interior thereof,
   said grommet means having a dependent end portion defining an aperture sized to perimetrically define a relatively large area of said workpiece substrate exposable to said electrolyte and a sealed perimetric interface thereabout,
   means for positioning said grommet means in operative abutting relation with said workpiece substrate,
   the improvement comprising,
   means for delivering a stream of electrolyte to the dependent end of said grommet means,
   means for connecting said electrolyte stream delivery means to a source of electrical potential of one polarity and said workpiece substrate to a source of electrical potential of opposite polarity to permit deplating of said portion of said thin metal coating exposed to said electrolyte from said workpiece substrate,
   a thin planar mask intermediate said workpiece substrate surface and the dependent end of said grommet means,
   said mask being of essentially non-compressible electrolyte impermeable material having an aperture therein of relatively small area compared to that of the aperture in said grommet means and perimetrically contoured to define an exposed area of said thin metal coating to be subjected to said electrolyte, and
   an electrolyte impermeable adhesive coating on one surface of said mask for removably securing said mask to the substrate with the perimetric edges of said mask aperture adhesively secured in electrolyte-tight relation with said thin metal layer to precisely define the area thereof to be exposed to said electrolyte,
   said mask being sized to be engaged by the dependent end portion of said grommet means at a location remote from said relatively small aperture therein to prevent escape of electrolyte from said electrolyte container.

2. The improvement as set forth in claim 1 wherein said mask includes a peripheral adhesive-free segment located remote from the aperture therein to facilitate removal of said mask from said substrate.

* * * * *